(12) United States Patent
Subramaniam et al.

(10) Patent No.: US 9,994,601 B2
(45) Date of Patent: Jun. 12, 2018

(54) DEPOLYMERIZATION OF LIGNIN USING METAL INCORPORATED MESOPOROUS SILICATE CATALYSTS

(71) Applicant: University of Kansas, Lawrence, KS (US)

(72) Inventors: Bala Subramaniam, Lawrence, KS (US); Anand Ramanathan, Lawrence, KS (US); Kakasaheb Y. Nandiwale, Lawrence, KS (US); Andrew M. Danby, Lawrence, KS (US); Raghunath V. Chaudhari, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days. days.

(21) Appl. No.: 15/355,507

(22) Filed: Nov. 18, 2016

(65) Prior Publication Data
US 2017/0145043 A1    May 25, 2017

Related U.S. Application Data

(60) Provisional application No. 62/257,580, filed on Nov. 19, 2015.

(51) Int. Cl.
| | | |
|---|---|---|
| *C10G 1/08* | (2006.01) | |
| *C08H 7/00* | (2011.01) | |
| *C07G 1/00* | (2011.01) | |
| *C07D 207/34* | (2006.01) | |
| *C07C 37/52* | (2006.01) | |
| *C07C 67/00* | (2006.01) | |
| *C07C 41/18* | (2006.01) | |
| *C07D 307/24* | (2006.01) | |
| *C07D 307/60* | (2006.01) | |
| *C07C 45/67* | (2006.01) | |
| *C07C 45/51* | (2006.01) | |
| *C07C 51/00* | (2006.01) | |

(52) U.S. Cl.
CPC .............. *C07G 1/00* (2013.01); *C07C 37/52* (2013.01); *C07C 41/18* (2013.01); *C07C 45/51* (2013.01); *C07C 45/673* (2013.01); *C07C 51/00* (2013.01); *C07C 67/00* (2013.01); *C07D 207/34* (2013.01); *C07D 307/24* (2013.01); *C07D 307/60* (2013.01); *C08H 6/00* (2013.01); *C10G 1/086* (2013.01); *C10G 2300/1014* (2013.01)

(58) Field of Classification Search
CPC ... C08H 6/00; C10G 1/086; C10G 2300/1014
See application file for complete search history.

(56) References Cited

U.S. PATENT DOCUMENTS

| | | |
|---|---|---|
| 8,299,310 B2 | 10/2012 | Zmierczak et al. |
| 9,051,244 B2 | 6/2015 | Dhepe et al. |
| 9,233,944 B2 | 1/2016 | Subramaniam et al. |

OTHER PUBLICATIONS

Pineda et al., Heterogeneously catalyzed lignin depolymerization, Appl Petrochem Res, Jun. 3, 2016.
Liu et al., Catalytic Fast Pyrolysis of Lignocellulosic Biomass, Chemical Society Reviews 43, May 7, 2014.
Deepa et al., Lignin Depolymerization into Aromatic Monomers over Solid Acid Catalysts, ACS Catal. 5, Dec. 1, 2014, pp. 365-379.
Kong et al., Direct Production of Naphthenes and Paraffins from Lignin, Chem. Commun., DOI: 10.1039/C5CC06828B., Sep. 28, 2015.
Ramanathan et al., Synthesis and characterization of Zirconium incorporated ultra large pore mesoporous silicate, ZrKIT-6, Microporous and Mesoporous Materials 167, Sep. 18, 2012, pp. 207-212.
Ramanathan et al., Novel zirconium containing cage type silicate (Zr-KIT-5): An efficient Friedel-Crafts alkylation catalyst, Chemical Engineering Journal 278, Dec. 3, 2014, pp. 113-121.
Pan et al., Synthesis and Dehydration Activity of Novel Lewis Acidic Ordered Mesoporous Silicate: Zr-KIT.6, Ind. Eng. Chem. Res. 52, Sep. 3, 2013, pp. 15481-15487.
Nandiwale et al., Lignin Depolymerization into Aromatic Monomers over Acidic Mesoporous Silicates, Presentation at the 2016 AIChE Annual Meeting, San Francisco, CA, Nov. 16, 2016.
Nandiwale et al., Lignin Depolymerization into Aromatic Monomers over Novel Zirconium Incorporated Mesoporous Silicates, Poster at ISCRE 24 Foundations and Vistas of Chemical Reaction Engineering, Minneapolis, MN, Jun. 13, 2016.

*Primary Examiner* — Robert Havlin
(74) *Attorney, Agent, or Firm* — Bell & Manning, LLC (57) ABSTRACT

Provided is a process for depolymerizing lignin, the process comprising exposing a liquid feed comprising lignin and a solvent to a metal-incorporated solid mesoporous silicate catalyst under conditions sufficient to depolymerize the lignin to produce one or more aromatic monomers.

14 Claims, 8 Drawing Sheets

DEPOLYMERIZATION OF LIGNIN USING METAL INCORPORATED MESOPOROUS SILICATE CATALYSTS

CROSS-REFERENCE TO RELATED APPLICATIONS

The present application claims priority to U.S. Provisional Patent Application No. 62/257,580 that was filed Nov. 19, 2015, the entire contents of which are hereby incorporated by reference.

REFERENCE TO GOVERNMENT RIGHTS

This invention was made with government support under grant number 2011-10006-30362 awarded by the United States Department of Agriculture and under grant number 1539105 awarded by the National Science Foundation. The government has certain rights in the invention.

BACKGROUND

Currently, the paper and pulp industry generates approximately 50 million tons of kraft lignin.[1] In 2014, 125 million liters of cellulosic ethanol were produced commercially in the United States, meeting the volume mandated by the Renewable Fuel Standard for the first time. In 2016, this production is expected to increase to 780 million liters per year. Significantly, for every liter of cellulosic ethanol produced, approximately 0.5-1.5 kg of lignin will be co-generated depending on the nature of lignocellulose used in the process.

The controlled deconstruction of lignin into aromatic platform chemicals and high-octane fuel additives is essential for ensuring the economic viability of the next generation of cellulosic ethanol bio-refineries.[2,3] However, lignin valorization remains a challenge due to its inherent heterogeneity, recalcitrance, diversity of inter-aromatic ring linkages, and complex three-dimensional polymeric structure composed of C—C and C—O bonds.[2-4]

In this context, a number of catalytic and thermochemical approaches for lignin depolymerization have been explored. Hydrogenolysis of lignin involving simultaneous depolymerization and hydrogenation have been carried out over heterogeneous metal catalysts with externally added $H_2$.[5,6,7] Supported metal catalysts such as Pd/C[8]; H-BEA-35/Raney Ni[9]; Ni/C[10], Pt/$Al_2O_3$[11]; and requiring an external hydrogen donor have been used for lignin deconstruction. In these experiments, at 150-300° C., lignin is reported to yield 50% aromatic monomers. Lignin depolymerization over Ni/C[12,13] and Pt/C[14] catalysts have been studied, where the catalyst enables in situ production of hydrogen from methanol[12,13] or formic acid[14] solvent. Catalysts such as methylrhenium trioxide,[15] and Pd/γ-$Al_2O_3$,[16] ionic liquid,[17] MgO,[18] perovskite-type oxide and CuO/$Fe_2(SO_4)_3$/NaOH[20] have been used to catalyze lignin depolymerization in the presence of $H_2O_2$ or $O_2$.

Homogeneous metal complexes and salts of Ru, Mn and CO can depolymerize lignin models and lignin.[21-25] Rahimi et al.[26] developed metal-free oxidation strategies for lignin and lignin model compounds.

Recently, alkaline catalysts, such as NaOH, KOH, CsOH etc. have been used in a base-catalyzed depolymerization (BCD) of lignin into aromatic monomers.[27-30] The main drawbacks of BCD are low selectivity towards aromatics, use of harsh reaction conditions, requirement of a neutralization step and reactor corrosion.[31] To overcome this, some solid base catalysts such as porous metal-oxides hydrotalcites,[32,33] Ni-supported layered double hydroxide hydrotalcite (Ni-HTC)[34], and nitrate-intercalated hydrotalcite[6] have been employed to depolymerize lignin.

Most reported studies employ model lignin compounds such as phenolic monomers and dimers. While these studies are useful in promoting a fundamental understanding of bond cleavage mechanisms with specific catalysts, they are not directly applicable to the deconstruction of real lignin.[2] Several strategies for the deconstruction of polymeric lignin have been reported recently using hydrodeoxygenation[35] and thermal catalytic depolymerization[31].

SUMMARY

Provided are processes for depolymerizing lignin. In embodiments, a process for depolymerizing lignin comprises exposing a liquid feed comprising lignin and a solvent to a metal-incorporated solid mesoporous silicate catalyst under conditions sufficient to depolymerize the lignin to produce one or more aromatic monomers.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Provided are processes for depolymerizing lignin. The present processes involve the use of metal-incorporated solid mesoporous silicate catalysts and the natural biopolymer itself, rather than a simplified model compound of lignin. At least some embodiments are able to provide high yields of aromatic monomer products as well as reduced formation of high molecular weight products, e.g., those produced from repolymerization of the monomers. Moreover, by contrast to conventional approaches to lignin depolymerization, the present processes employ mild conditions, benign solvents and do not require the use of any externally added reactants such as $H_2$.

An embodiment of the process includes exposing a liquid feed including lignin and a solvent to a metal-incorporated solid mesoporous silicate catalyst under conditions sufficient to depolymerize the lignin to produce one or more aromatic monomers. The one or more aromatic monomers may be collected from the processed liquid feed.

Lignin is an amorphous three dimensional polymer consisting of phenylpropane structures. Lignin is formed from three monolignol monomers, p-coumaryl alcohol, coniferyl alcohol and sinapyl alcohol, which undergo enzymatic polymerization resulting in a complex polymer linked via eleven types of covalent bonds. The β-O-4 linkage is the most common bond accounting for between 30% and 60% of all linkages.

The lignin may be characterized by the biomass source from which the lignin is extracted. Illustrative biomass sources include forestry product or waste, agricultural product or waste, municipal product or waste, etc. In addition to lignin, the biomass source may include other biopolymers such as cellulose and hemicellulose. However, in embodiments, the liquid feed is substantially free of any other biopolymers other than lignin. By "substantially free" it is meant that the liquid feed is completely free of such other biopolymers or such other biopolymers are present in amounts which are small enough so as to have no material effect in the present processes.

The lignin may also be characterized by the procedure used to extract the lignin. Lignin may be extracted from the biomass source using several techniques, including organosolv, steam explosion, dilute acid hydrolysis, alkali extraction and wet oxidation procedures. Commercial sources of lignin may be used, e.g., from TCI Chemicals. The lignin used in the Examples below may be referred to as "dealkaline lignin."

After extraction, the lignin is dissolved using a solvent to form the liquid feed. A variety of solvents may be used, provided the solvent is able to dissolve the lignin. In embodiments, the solvent is an organic solvent such as methanol or acetonitrile. Other low molecular weight alcohols may be used, e.g., propanol. Combinations of different organic solvents may be used. In some embodiments, the organic solvent(s) is combined with water. Illustrative amounts of water include those in the range of from about 10 v/v % to about 25 v/v %, wherein v/v % is (volume of water/total volume of solvent)*100. This includes embodiments in which the amount of water is in the range of from about 12 v/v % to about 22 v/v %, or from about 15 v/v % to about 20 v/v %. The particular composition of the solvent (organic solvent(s) type, use of water, relative amounts) may be selected in order to tune acidity. For example, water and low molecular weight alcohols can form Brönsted acids via their reaction with Lewis acids. (See Huber, Chem. Rev. 115, 11559-11624 (2015), which is hereby incorporated by reference in its entirety.) Various amounts of lignin may be used in the liquid feed. The particular amount depends on the solubility of the lignin used at the selected reaction temperature. Various amounts up to the amount at saturation concentration may be used. "Saturation concentration" is the concentration of lignin above which concentration any additional lignin added does not dissolve in the selected solvent and selected reaction temperature.

As noted above, the catalyst is a solid mesoporous silicate including a metal (M) incorporated therein. Various metal-incorporated solid mesoporous silicate catalysts may be used. The terms "metal-incorporated" and the like refer to the direct incorporation of the metal atoms into the silicate lattice structure such that the metal atoms replace silicon atoms. The metal atoms may be substantially completely incorporated into the silicate lattice structure. The term "substantially" has a meaning analogous to that described above with respect to "substantially free." This is by contrast to materials made using grafting and impregnation approaches which create active species without direct incorporation of the metal atoms into the silicate lattice structure. Evidence of metal-incorporation and the extent of incorporation may be derived from small-angle X-ray scattering (SAXS) pattern analysis (to assess modification of the unit-cell parameters of the silicate lattice structure), elemental analyses (to assess amount of metal incorporation) as well as ultraviolet-visible spectroscopy (to determine existence of metal-oxygen bonding and bond structure).

Various metals may be used, including transition metals and metalloids. Combinations of different metals may be used. Illustrative metals include 4d transition metals such as Zr and Nb; 5d transition metals such as W; and metalloids such as Al.

The catalyst may be characterized by its lattice structure and symmetry (e.g., as determined from SAXS). In embodiments, the catalyst is characterized by a cubic structure with Ia3d symmetry (known as "KIT-6") or a cubic structure with Fm3m symmetry (known as "KIT-5").

The catalyst may be further characterized by properties such as specific surface area, pore volume and pore diameter. The Brunauer-Emmett-Teller (BET) technique may be used to determine specific surface area (i.e., $S_{BET}$). The Barret-Joyner-Halenda (BJH) technique may be used to determine pore volume (i.e., $V_{p,\,BJH}$) and pore diameter (i.e., $d_{p,\,BJH}$). In embodiments, the catalyst is characterized by a pore diameter ($d_{p,\,BJH}$) in the range of from 2 nm to about 20 nm. This includes embodiments in which the pore diameter is in the range of from 5 nm to about 15 nm, or from 6 nm to about 12 nm. These pore diameters distinguish the present mesoporous catalysts from microporous catalysts, the latter which have smaller pore sizes.

The catalyst may be further characterized by the ratio of Si to metal (M) atoms, i.e., Si/M. In embodiments, the Si/M ratio is in the range of from about 5 to about 400. This includes embodiments in which the Si/M ratio is in the range of from about 10 to about 300, from about 10 to about 200, from about 10 to about 100, or from about 15 to about 50. Related to the Si/M ratio, the catalyst may be further characterized by its total acidity. Total acidity may be determined using temperature-programmed desorption of ammonia ($NH_3$-TPD) according to the procedure described in the Examples, below. In embodiments, the total acidity is at the substantial maximum value for the selected metal. By "substantial maximum" it is meant that the value of the total acidity is at its maximum value or a value which is close enough to the maximum value as to have about the same effect in the present processes. The substantial maximum value can also be determined using $NH_3$-TPD. In embodiments, the total acidity is in the range of from about 0.05 to about 1.0 mmol $NH_3$/g. This includes embodiments in which the total acidity is in the range of from about 0.08 to about 1.0 mmol $NH_3$/g, or from about 0.10 to about 0.80 mmol $NH_3$/g.

The catalyst may be characterized by its acidity type. Acidity types include Lewis acidity (i.e., exhibiting the ability to accept an electron pair) as well as Brönsted acidity (i.e., exhibiting the ability to provide a proton in solution). In embodiments, the catalyst is characterized as being Lewis acidic, by which it is meant it includes active sites having the ability to accept electron pairs. In embodiments, the catalyst is characterized as being predominately Lewis acidic, by which it is meant that predominantly all the active sites exhibit Lewis acidity versus another acidity type (e.g., Brönsted acidity). The acidity type may refer to the intrinsic acidity of the catalyst. The term "predominantly" has a meaning analogous to that described above with respect to "substantially free." As further described in the Examples, below, it has been found that such predominant Lewis acidity can suppress the amount of repolymerization of aromatic monomers during the depolymerization process. This is critically important to maximizing the efficiency and cost-effectiveness of bio-refineries.

The particular catalyst, its characteristics and properties may be selected to provide a desired total yield of aromatic monomers and/or yield of a particular type(s) of aromatic monomers. Illustrative metal-incorporated solid mesoporous silicate catalysts include M-KIT-6 and M-KIT-5, wherein M is selected from Zr, Nb, W, Al, or combinations thereof. In embodiments, the metal-incorporated solid mesoporous silicate catalyst is Zr-KIT-6 or Zr-KIT-5. The catalysts may be characterized by various combinations of specific surface area, pore volume, pore diameter, Si/M ratio, total acidity and acidity type as described above.

Methods for making the metal-incorporated solid mesoporous silicate catalysts are described in the Examples below.

Various ratios of lignin to catalyst may be used. The ratio may be selected to provide a desired total yield of aromatic monomers. In embodiments, the ratio is in the range of from about 1:1 to about 15:1. This includes ratios in the range of from about 5:1 to 15:1 or from about 10:1 to about 15:1.

Figure 1:
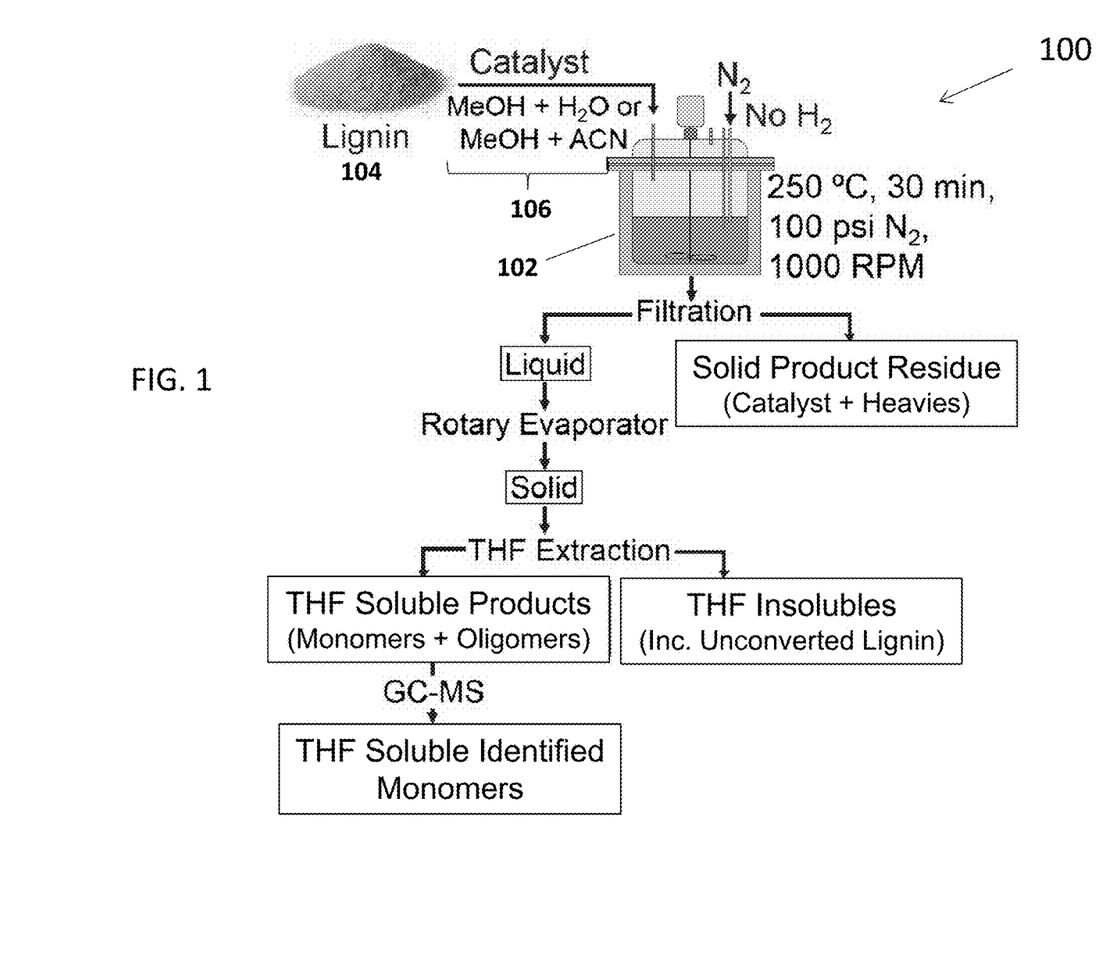
FIG. 1 is a schematic representation of the catalytic depolymerization of lignin according to an illustrative embodiment.

The present processes may be carried out using a variety of reactor systems. As illustrated in FIG. 1, the reactor system may be a batch reactor system 100 including a reaction chamber 102. In the illustrative embodiment, the reaction chamber 102 is a stirred reaction chamber commercially available from Parr Instrument Company, which allows a liquid feed containing the lignin 104 and the solvent 106 to be stirred in the reaction chamber loaded with catalyst during the depolymerization. The reaction chamber 102 is configured to provide a selected reaction atmosphere and a selected reaction temperature. As further illustrated in FIG. 1, the processed liquid feed can be collected and analyzed for the production of aromatic monomers. Various configurations of the batch reactor system 100 may be used. Other reactor systems may be used, e.g., continuous flow reactor systems in which the liquid feed is handled via a continuous, flowing stream.

By "conditions," as that term is used with respect to the present processes, can refer to the reaction atmosphere, the reaction temperature, the stirring rate, the reaction time, etc. These conditions may be adjusted to achieve a desired total yield of aromatic monomers and/or a desired yield of a particular aromatic monomer. The reaction atmosphere may be an inert atmosphere, e.g., $N_2$ gas. In embodiments, the reaction atmosphere is substantially free of components which may participate in the depolymerization reactions, e.g., $H_2$, $O_2$, or $H_2O_2$. The term "substantially free" has the same meaning as described above with respect to the liquid feed. Thus, embodiments of the present processes may be distinguished from conventional processes requiring the addition of externally added reactants such as $H_2$, $O_2$ or $H_2O_2$. Illustrative reaction temperatures include those in the range of from about 100° C. to about 300° C., including from about 150° C. to about 300° C., or from about 200° C. to about 300° C. Illustrative stirring rates include those in the range of from about 400 rpm to about 1500 rpm. Illustrative reaction times include those in the range of from about 1 min to about 90 min, including from about 10 min to about 60 min, or from about 10 min to about 45 min. Due to the disclosed reaction temperatures and use of a liquid feed, embodiments of the present processes may be distinguished from catalytic pyrolysis processes employing much higher reaction temperatures and gaseous feeds.

As further described in the Examples below, at least in some embodiments, the present processes are able to achieve high amounts of lignin conversion. In embodiments, the present processes achieve a lignin conversion of at least 50%, at least 60%, at least 70%, at least 75%, at least 80%, at least 85% or at least 90%. Lignin conversion may be defined as ((weight of lignin charged in reactor−weight of THF insolubles)/(weight of lignin charged in reactor))*100. (See "$X_L$" in Table 4, below.)

As further described in the Examples below, at least in some embodiments, the present processes are able to achieve high yields of aromatic monomers. The aromatic monomers can include those shown in FIG. 2B and in Table 3, below. In embodiments, the present processes achieve a yield of THF soluble products of at least 25% by weight, at least 30% by weight, at least 35% by weight, at least 45% by weight, at least 55% by weight, or at least 65% by weight. Yield of THF soluble products may be defined as ((weight of THF soluble fraction−weight of identified monomers)/(weight of lignin charged in reactor))*100. (See "THF soluble products" in Table 4, below.) These yields may be obtained in other organic solvents besides THF.

As further described in the Examples below, at least in some embodiments, the present process also exhibits reduced amounts of high molecular weight products, e.g., as compared to the conventional catalyst H-ZSM-5. (See also, FIG. 5.) The amount of high molecular weight products may be quantified via the yield of insoluble products precipitating from the reaction mixture as described in the Examples, below (i.e., "solid product residue" in Table 4, below). In embodiments, the yield of these insoluble products is less than about 35% by weight, less than about 30% by weight, less than about 25% by weight, less than about 20% by weight, less than about 15% by weight, or less than about 10% by weight. Yield of solid product residue may be defined as ((weight of insoluble material after reaction−weight of initial catalyst)/(weight of lignin charged in reactor))*100. By comparison, in the Examples below, the conventional catalyst H-ZSM-5 was found to produce over 40% by weight of such insoluble products. Reduced amounts of high molecular weight products and the ability to suppress repolymerization of formed monomers are significant advantages for improving the efficiency and cost-effectiveness of bio-refineries.

The yields described above may refer to a particular set of reaction conditions, e.g., lignin:catalyst ratio of about 15:1, water/methanol solvent at about 1/5 v/v, reaction temperature of about 250° C., reaction time of about 30 minutes, stirring rate of about 1000 rpm, and about 0.7 MPa of $N_2$ at ambient temperature.

EXAMPLES

Experimental
Materials
Dealkaline lignin was procured from TCI Chemicals (Product No. L0045). Tetrahydrofuran (THF, 99.9%), acetonitrile (99.9), methanol (99.9), and dimethylformamide (DMF, 99.9%) were purchased from Thermo Fisher Scientific. Tetraethyl orthosilicate (TEOS 98%), Zirconium (IV) oxychloride octahydrate (99.5%), Zirconium (IV) propoxide (70 wt. % in 1-propanol), and Pluronic P123 (EO20-PO70-EO20) were procured from Aldrich.

The commercial zeolites: H-FER, H-MOR, H-Beta, H-USY and H-ZSM-5 with variation in Si/Al ratios were procured from Zeolyst International. The zeolite samples were calcined at 550° C. for 6 h and a protonic form of these samples was used for catalytic evaluation.

Catalyst Synthesis

Synthesis of Zr-KIT-6 catalysts Si/Zr ratios of 20, 40 and 100, designated as Zr-KIT-6(20), Zr-KIT-6(40) and Zr-KIT-6(100), respectively, were prepared as reported previously. (See Pan Q, et al., *Industrial & Engineering Chemistry Research*. Nov. 6, 2013; 52(44):15481-15487 and Ramanathan A, et al., *Micropor Mesopor Mat*. Feb. 2 2013; 167: 207-212, each of which is hereby incorporated by reference in its entirety.) In a typical synthesis, 5.0 g of triblock copolymer Pluronic P123 was dissolved in 175 ml of 0.5 M HCl solution at 35° C. After complete dissolution, 5.0 g of n-butanol was added, and the mixture was stirred for another 1 h. Next, 10.6 g of TEOS and the desired amount of Zirconium (IV) propoxide were added, and the mixture was again stirred at 35° C. for 18 h. The mixture was transferred to a Teflon lined SS autoclave and subjected to hydrothermal treatment at 98° C. for 48 h under static conditions. The solid product was obtained after filtration without washing, and dried overnight at 100° C. The sample was then calcined at 550° C. for 5 h in air.

Zr-KIT-5 with variation in Si/Zr ratios of 20, 40 and 100 (designated as Zr-KIT-5(20), Zr-KIT-5(40) and Zr-KIT-5(100), respectively) were synthesized in accordance with the reported procedure. (See Ramanathan A, et al., *Chem Eng J*. Oct. 15, 2015; 278:113-121, which is hereby incorporated by reference in its entirety.)

Catalyst Characterization

Low temperature (−196° C.) nitrogen sorption isotherms of catalysts were recorded with a Quantachrome Autosorb-6B instrument. The specific surface area and pore diameter of samples were calculated using the Brunauer-Emmett-Teller (BET) and Barret-Joyner-Halenda (BJH) methods, respectively. The total pore volume of the catalyst sample was estimated based on the amount of nitrogen adsorbed at $P/P_0=0.98$.

The total acidities of all catalysts were measured by temperature-programmed desorption of ammonia ($NH_3$-TPD) using Micromeritics AutoChem (2910, USA) equipped with a Thermal Conductivity Detector (TCD). Prior to the measurements, the sample was dehydrated at 250° C. in flowing helium (10 sccm).[38] The temperature was then decreased to 100° C. and Ammonia was allowed to adsorb by exposing the sample to a gas He stream containing 9.98 vol % $NH_3$ flowing at 10 sccm for 30 min. The sample was then flushed with helium (10 sccm) for another 30 min to remove any physisorbed ammonia. The $NH_3$ desorption was carried out in helium flow by increasing the temperature to 550° C. at a heating rate of 10° C./min.

Catalytic Deconstruction of Lignin

As illustrated in FIG. 1, the catalytic depolymerization of lignin was carried out in a 300 mL batch reactor (Parr Instruments). In a typical experiment, the reactor was loaded with the catalyst and lignin dissolved in a solvent consisting of either acetonitrile+methanol or methanol+water. The reactor was sealed, purged with $N_2$ three times, and pressurized with 0.7 MPa of $N_2$ at ambient temperature. The reactor was heated to 250° C. with initial stirring at 100 rpm. The temperature was attained within 25 min and the stirring was then increased to 1000 rpm, which was used as the zero reaction time. After the desired reaction time, the heating and stirring was stopped, and the reactor was allowed to cool in air for 5 min before being quenched with an ice-water mixture to room temperature which lasted another 10 min.

Analysis of Gas, Solution and Solid Phases of Reaction Mixture

As illustrated in FIG. 1, the solid obtained after reaction was separated from the liquid by filtration. The solvents from the liquid product mixture were removed by Buchi™ rotavapor. The obtained solid was dissolved in THF and filtered to obtain THF insolubles.

The liquid product mixture obtained after reaction was filtered through a 0.22 μm PVDF syringe filter and analyzed by Agilent 7890A GC coupled to a 5975C MS, HP-INNO-WAX column with helium as the carrier gas (1 std cm³/min), an inlet temperature of 250° C., and an injection volume of 1 μL. The oven temperature was initially held at 40° C. for 5 min; then increased at a rate of 10° C. per minute to 220° C.; then held at this temperature for an additional 20 min. Masses were scanned from 20 to 500 Da, and retention times and MS fragmentation patterns were matched with external standards.

The gas obtained after reaction was collected in a sampling bag and analyzed by GC-FID. The lignin and THF soluble depolymerized product were analyzed by Gel Permeation Chromatography (GPC), using an Agilent 1260 Infiniti GPC system fitted with a refractive index detector. Two columns were used in series at 40° C.: a 300 mm Polargel-M, followed by a 300 mm Polargel-L; and the samples were eluted with DMF at a flow rate of 1.0 ml/min. Polymethyl methacrylate (PMMA) standards were used for calibration.

The CHN analysis of lignin and depolymerized products were performed using a Perkin Elmer Series II 2400 CHN/O Analyzer.

Results and Discussion

The physical characteristics of the commercial zeolites is provided in Table 1, below.

TABLE 1

Physical characteristics of commercial zeolites.

| Zeolite[a] | Commercial name | $SiO_2/Al_2O_3$[b] | $S_{BET}$ $(m^2/g)$[c] | Total acidity $(mmol/g)$[d] |
|---|---|---|---|---|
| H-FER (27.5) | CP 914 | 55 | 400 | 0.41 |
| H-MOR (45) | CBV 90A | 90 | 500 | 0.47 |
| H-Beta (150) | CP 811C | 300 | 620 | 0.70 |
| H-Beta (19) | CP 814C | 38 | 710 | 0.88 |
| H-Beta (12.5) | CP 814E | 25 | 680 | 1.03 |
| H-USY (40) | CBV 780 | 80 | 780 | 0.16 |
| H-USY (30) | CBV 760 | 60 | 720 | 0.32 |
| H-USY (6) | CBV 712 | 12 | 730 | 0.81 |
| H-USY (2.6) | CBV 600 | 5.2 | 660 | 0.90 |
| H-ZSM-5 (140) | CBV 28014 | 280 | 400 | 0.15 |
| H-ZSM-5 (25) | CBV 5524G | 50 | 425 | 0.73 |
| H-ZSM-5 (11.5) | CBV 2314 | 23 | 425 | 0.97 |

[a] Bracketed number denotes Si/Al ratio of catalyst,
[b] $SiO_2/Al_2O_3$ ratio provided by the manufacturer,
[c] $S_{BET}$ = specific surface area provided by the manufacturer,
[d] Total acidity of catalyst was determined with $NH_3$-TPD.

The physical characteristics of the KIT-based catalysts is provided in Table 2, below.

TABLE 2

Physical characteristics of KIT-based catalysts.

| Catalyst | $S_{BET}$ (m²/g)[a] | Total acidity (mmol/g)[b] |
|---|---|---|
| Si-KIT-6 | — | 0.01 |
| Zr-KIT-6 (100) | 980 | 0.19 |
| Zr-KIT-6 (40) | 881 | 0.31 |
| Zr-KIT-6 (20) | 810 | 0.50 |
| Zr-KIT-5 (100) | 1018 | 0.16 |
| Zr-KIT-5 (40) | — | 0.32 |
| Zr-KIT-5 (20) | 970 | 0.64 |

[a] $S_{BET}$ = specific surface area,
[b] Total acidity of catalyst was determined with $NH_3$-TPD.

Quantification of Depolymerized Products

The products obtained after depolymerization of lignin were separated, quantified and characterized. After depolymerization, the resulting product mixture was filtered. The filter cake consisted of catalyst and solid product residue. The percentage of solid product residue was calculated after deducting the weight of catalyst charged at the start of reaction. The lignin used in the present study is not soluble in THF. Hence, the depolymerized products from this mixture were separated by dissolving in THF. The solid obtained after evaporating the solvent was dissolved in THF which was then subjected to filtration. The filter cake consists of THF insolubles (quantified after drying), and the filtrate liquid consists of THF soluble products. The percentage of THF soluble products was calculated on basis the solid recovered after evaporating THF.

Yield of Detectable Monomers

Figure 2A:
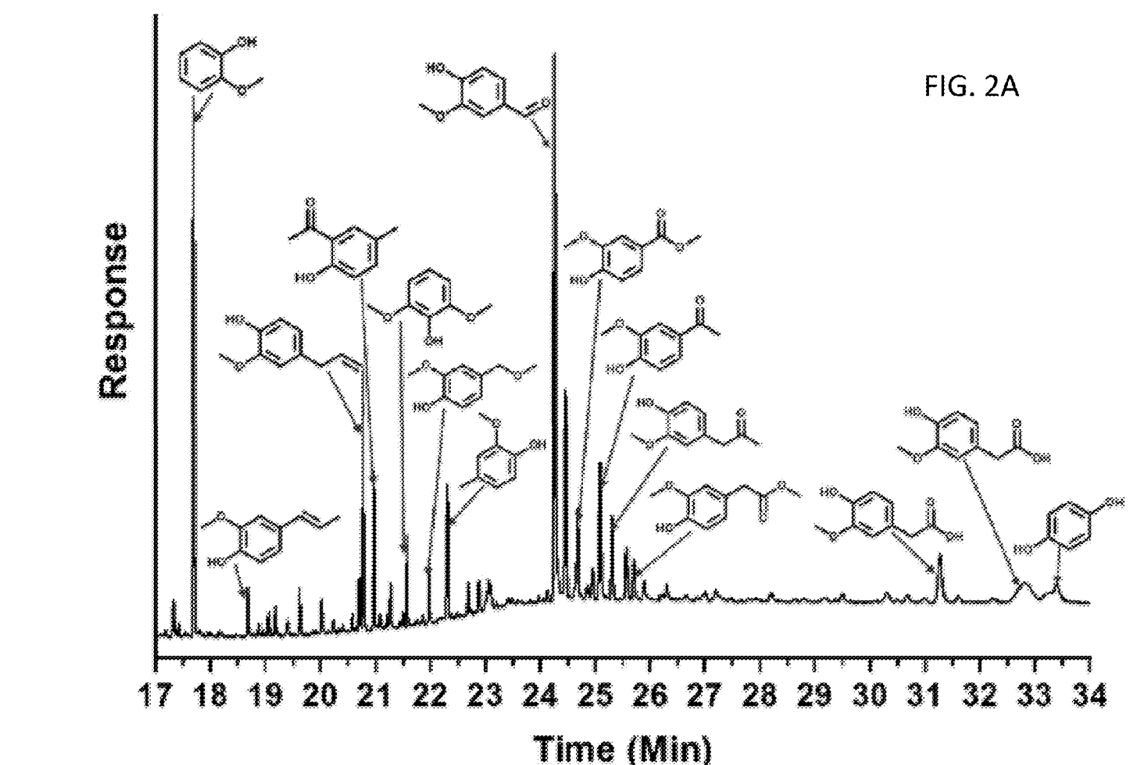
FIG. 2A shows a GC/MS spectrum of monomeric products obtained from the depolymerization of dealkaline lignin over a Zr-based mesoporous silicate catalyst.

The monomers produced in lignin depolymerization were identified and quantified. The liquid product mixture obtained after the reaction was filtered through a 0.22 μm PVDF syringe filter and analyzed by GC-FID and GC-MS. The m/z values observed in the fragmentation pattern of MS were compared using the NIST Mass Spectral Search Program and the identified monomers were matched with probabilities higher than 73%. About 15 monomers were confirmed by using external standards, and matching with fragmentation pattern and retention time. A sample GC chromatogram and the identified monomers is shown in FIG. 2A. The identified monomers are shown separately in FIG. 2B.

The quantity of identified monomers in the product mixture was calculated from the GC-FID data. The response factor of GC-FID was calculated by using the monomer standards. The standards of all of the identified monomers were not readily available. Hence, the average response factor obtained by using the available standards was used to quantify the other identified monomers. The identified monomers belonged to a class of monomeric species one would expect from the lignin. They also matched well with lignin products reported elsewhere[31]. The summation of all of the identified monomers is designated as THF soluble identified monomers. Not all of the THF soluble products could be detected by GC-FID, as the THF soluble products may contain dimers, trimers, sugar-derived monomeric species, and significant fractions of residual carbohydrates. After deducting the weight of THF soluble identified monomers (detected by GC-FID) from the total of the THF soluble products, the remaining fraction was designated as THF soluble unidentified monomers.

In order to check any gaseous products formed as a result of the lignin depolymerization, the gas sample obtained after reaction by cryogenic GC-TCD was analyzed. However, no gaseous products were detected in the sample. This confirms that catalytic lignin depolymerization under the reaction conditions described above does not form any gaseous products.

Evaluation of Catalytic Activity of Commercial Zeolites in Acetonitrile

Figure 3A:
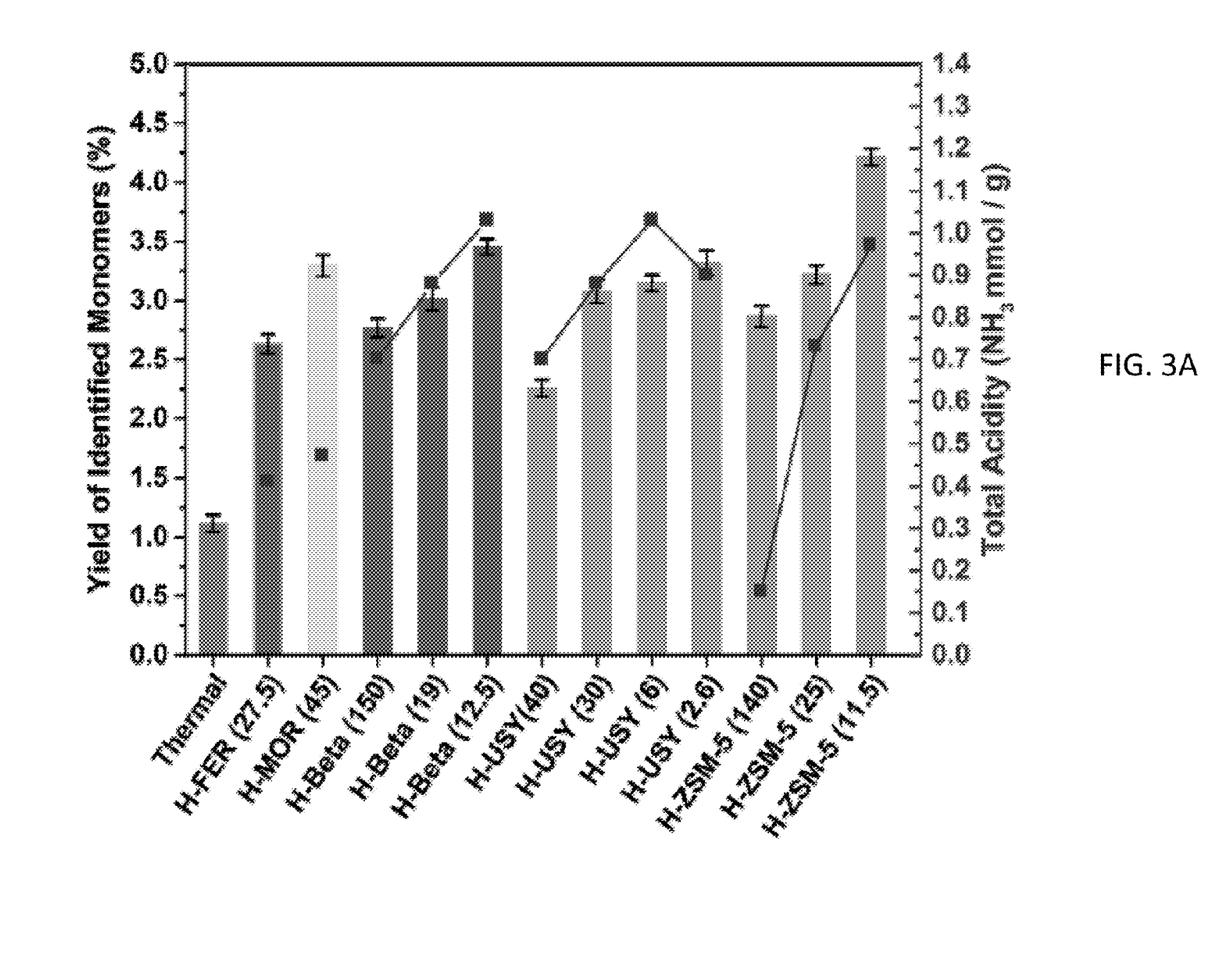
FIG. 3A shows the activity of commercial zeolites and FIG. 3B shows the activity of Zr-based mesoporous silicate catalysts towards lignin depolymerization using acetonitrile+methanol solvent. Reaction conditions: lignin (0.5 g), catalyst (0.5 g), acetonitrile+methanol (10+90 mL), 250° C., 30 min, 1000 rpm, 0.7 MPa of $N_2$ at ambient temperature.

FIG. 3A summarizes the activities of commercial zeolites and total acidities at identical reaction conditions. Different families of zeolites, including H-MOR, H-FER, H-Beta, H-USY and H-ZSM-5, along with differences in their Si/Al ratios (indicated in parentheses), were evaluated for lignin depolymerization. Within the same type of zeolite, a decrease in Si/Al ratio corresponded to an increase in the acidity of the zeolite. The thermal reaction, performed without catalyst, yielded only 1.1% THF soluble identified monomers. In contrast, the lowest yield of THF soluble identified monomers using a solid acid catalyst was 2.3%. Within the H-Beta, H-USY and H-ZSM-5 families of zeolites, the activity increased with total acidity. For instance, in the case of H-Beta, when the Si/Al ratio decreased from 150 to 12.5, the acidity increased from 0.7 to 1.0 mmol $NH_3$/g. This in turn was found to enhance the yield of identified monomers from 2.8 to 3.4%. Using the H-USY catalyst and increasing the total acidity from 0.16 to 8 mmol $NH_3$/g enhanced the yield of identified monomers from 2.3 to 3.3%.

Using an H-ZSM-5 catalyst and increasing the total acidity from 0.15 to 0.97 mmol $NH_3$/g enhanced the yield of identified monomers from 2.9 to 4.2%. However, across the different zeolites, there was no direct correlation between observed catalytic activity and total acidity. Among the investigated zeolites, H-ZSM-5 (Si/Al=11.5) displayed the highest activity, producing 4.2% identified monomers in acetonitrile and methanol solvent.

Activity Evaluation of Zr Based Mesoporous Catalysts in Acetonitrile

Figure 3B:
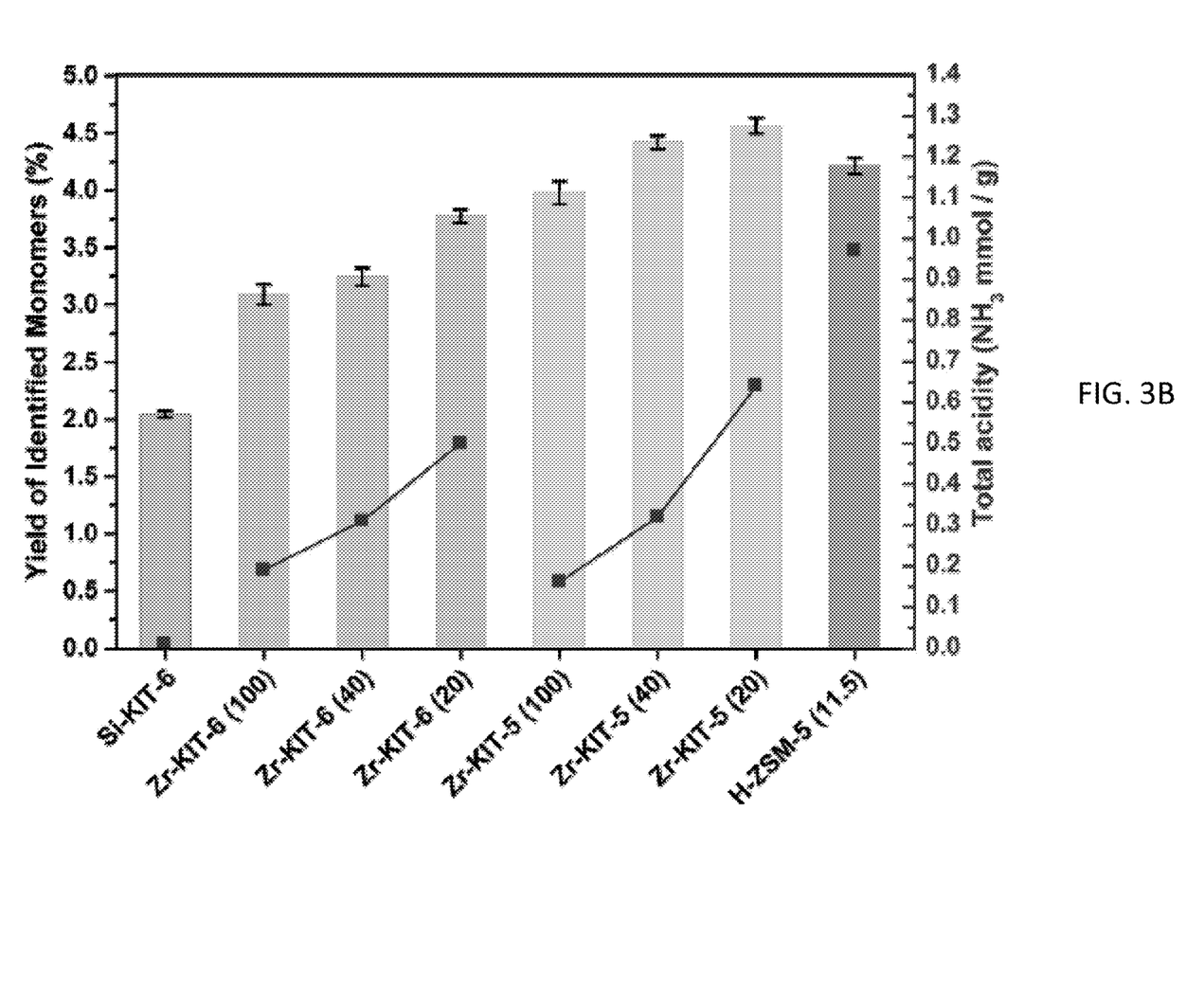

The activities of two groups of mesoporous silicates—Zr-KIT-5 and Zr-KIT-6—with different (Si/Zr) ratios were investigated. The activity data along with total acidity of these catalysts are presented in FIG. 3B. Increasing the acidity of Zr-KIT-6 from 0.2 to 0.5 mmol $NH_3$/g enhanced the identified monomer yield from 3.1 to 3.8%. A similar increase in identified monomers from 4.0 to 4.6% was observed over Zr-KIT-5 with an increase in acidity from 0.16 to 0.64 mmol $NH_3$/g. Although the total acidity of Zr-KIT-5(Si/Zr=20) (0.62 mmol $NH_3$/g) is lower than H-ZSM-5 (0.97 mmol $NH_3$/g), the amount of identified monomers over Zr-KIT-5 (20) (4.6%) is greater than that observed with H-ZSM-5 (4.2%). Two different solvent systems, methanol+acetonitrile and methanol+water, were tested for dissolving the lignin. Lignin depolymerization with methanol+acetonitrile solvent was observed to form acetamide at 250° C. in the presence of catalysts. Hence, further reactions were carried out with methanol+water (75+15 mL) solvent.

Evaluation of Catalytic Activity of Commercial Zeolites in Methanol

Figure 4A:
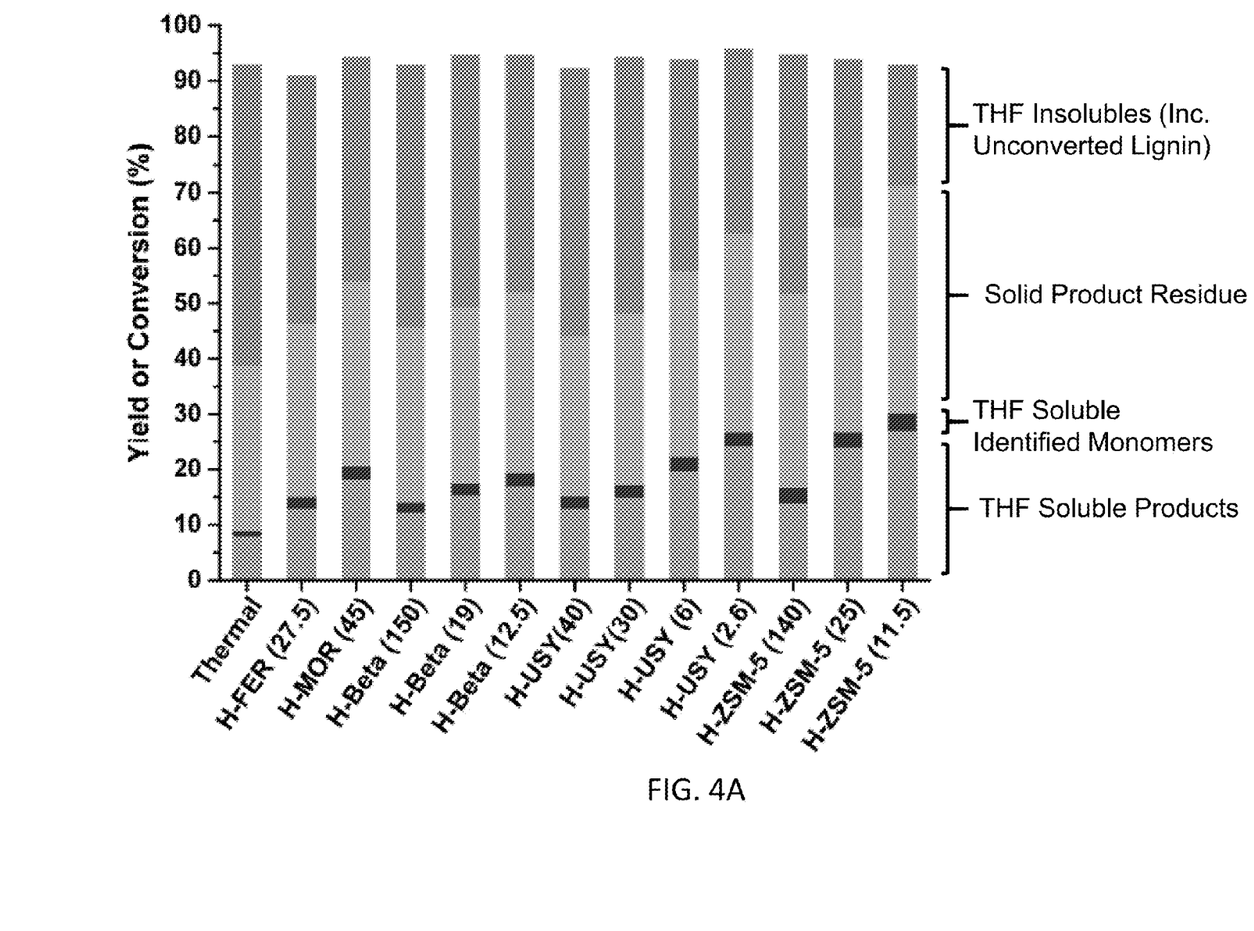
FIG. 4A shows the activity of commercial zeolites and FIG. 4B shows the activity of Zr-based mesoporous silicate catalysts towards lignin depolymerization using water+methanol solvent. Reaction conditions: lignin (1.5 g), catalyst (0.1 g), water/methanol (1/5 v/v), 250° C., 30 min, 1000 rpm, 0.7 MPa of $N_2$ at ambient temperature.
Figure 4B:
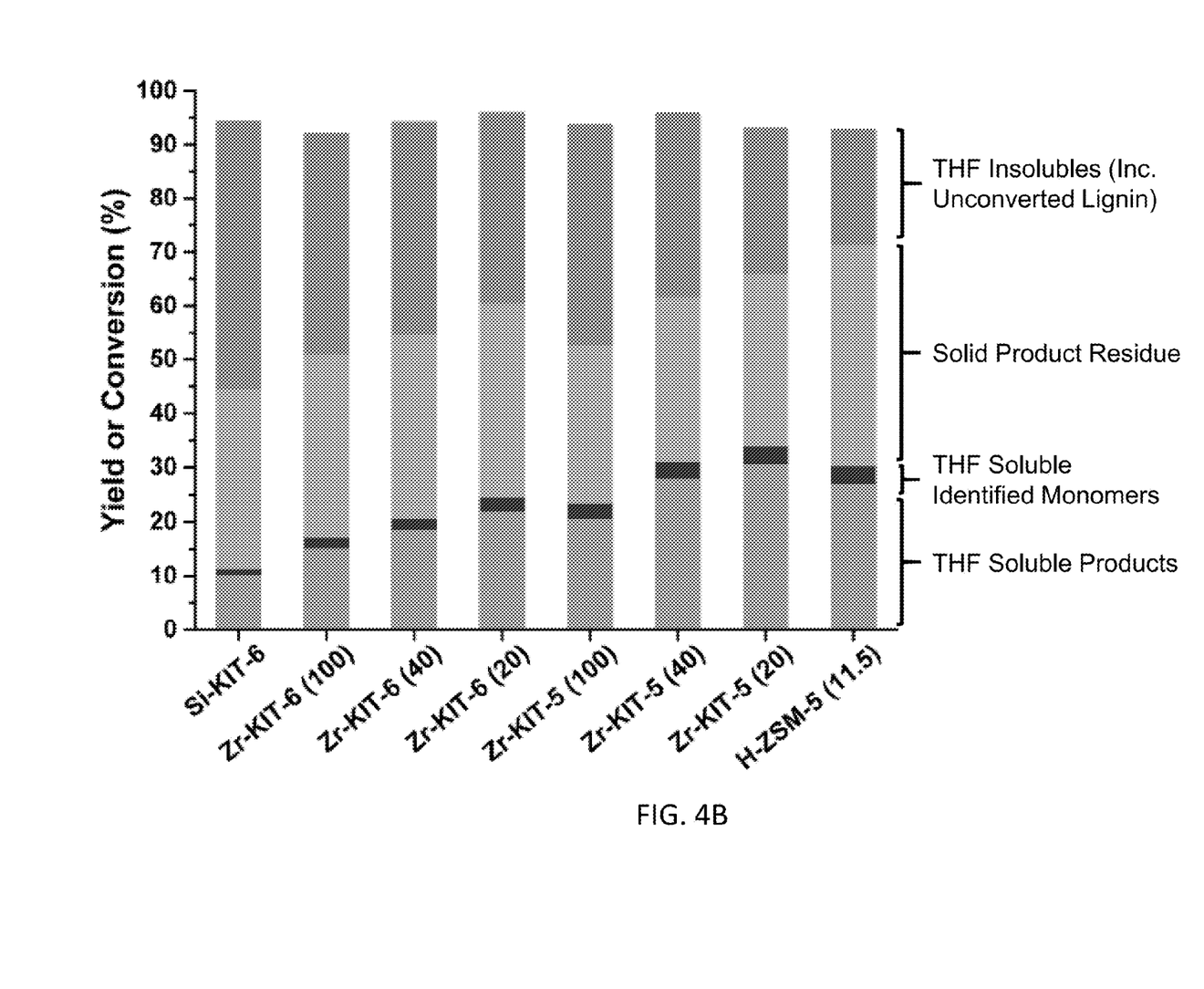

To test for possible aromatization of the methanol solvent, a blank reaction with methanol+water (75+15 mL) and H-ZSM-5 (0.1 g) catalyst was performed. No aromatic monomers were observed following reaction at 250° C. for 30 min. As shown in FIGS. 4A-4B, all the commercial zeolites along with Zr-based mesoporous silicates were evaluated with lignin (1.5 g), catalyst (0.1 g), and methanol+water (75+15 mL), at 250° C. for 30 min. A large amount of catalyst (1.5 g catalysts per 1.5 g of lignin) was used to benchmark literature data[31]. However, using an amount of catalyst equal to the amount of lignin would not be economically or industrially feasible. In addition, higher catalyst loading may result in the catalyst not being utilized to its fullest extent. Hence, it was decided to screen catalysts at lower catalyst loading (0.1 g catalyst per 1.5 g of lignin) rather than the reported (1.5 g catalyst per 1.5 g lignin).[31] Because dealkaline lignin is insoluble in THF, it could be used in the extraction of depolymerized products to avoid unreacted lignin contamination.[31] These results for H-ZSM-5 are consistent with those reported recently in the literature for this catalyst under identical conditions,[31] recognizing that the THF-soluble fraction contains oligomeric compounds in addition to aromatic monomers. FIG. 4A shows that the thermal depolymerization resulted in 8.0% of THF soluble unidentified products, 1.0% yield of identified monomers, and 29.9% yield of solid product residue. However, as shown in FIG. 4A, using the zeolite catalysts, the yield of THF soluble unidentified products varied from 13.0 to 27.1%; the yield of THF soluble identified monomers varied from 2.1 to 3.2%; and the yield of solid product residue varied from 31.5 to 41.0%. Yield of THF insolubles (including unconverted lignin) with thermal was 54%. However, the yield of THF insolubles was found to vary from 44.3 to 21.5% with catalyst. Mass balance was 95±5% in all of the experiments.

In particular, H-FER (27.5) was found to yield 13.0% of THF soluble unidentified products, 2.1% of THF soluble identified monomers, 31.5% solid product residue, and 44.3% THF insolubles (including unconverted lignin). Using H-MOR(45), the yields were 18.3%, 2.3%, 33.6% and 40%, respectively.

Decreasing the Si/Al ratio of H-Beta from 150 to 12.5 was found to increase the yields of THF soluble unidentified products (12.3-17%), THF soluble identified monomers (1.8-2.4%) and solid product residue (31.7-32.8%). However, the yield of THF insolubles (including unconverted lignin) decreased from 47.0 to 42.3%. This can be attributed to the increase in total acidities of H-Beta zeolites, which correlates with a decreasing Si/Al ratio. In the case of H-USY zeolites, when the Si/Al ratio decreased from 40 to 2.6, the yields of THF soluble unidentified products, THF soluble identified monomers, and solid product residue increased from 13% to 19.8%, from 2.2% to 2.6%, and from 29.0% to 35.8%, respectively. In contrast, the yield of THF insolubles (including unconverted lignin) was found to decrease from 42.3% to 33%, which may be due to an increase in the total acidity of the catalyst. Similarly, an increase in the yields of THF soluble unidentified products (from 14.0% to 27.1%), THF soluble identified monomers (from 2.7% to 3.2%), and solid product residue (from 35.0% to 41.0%) was obtained by decreasing the Si/Al ratio of H-ZSM-5 from 140 to 11.5. The yield of THF insolubles (including unconverted lignin) decreased from 43.0% to 21.5% over these different Si/Al ratios of H-ZSM-5 zeolites.

Thus, yields of THF soluble products and solid product residue were found to increase along with an increase in the total acidity within the H-Beta, H-USY and H-ZSM-5 families of zeolites. However, THF insolubles (including unconverted lignin) decreased when total acidity within same zeolite family increased. Overall trends in the yields of THF soluble products and solid product residues were found to be as follows: H-FER (27.5)<H-MOR (45)<H-Beta (12.5) <H-USY (2.6)<H-ZSM-5 11.5). Thus, H-ZSM-5 (11.5) was found to produce the highest yields of THF soluble unidentified products (27.1%), THF soluble identified monomers (3.2%), and solid product residue (41.0%); and the lowest (21.5%) yield of THF insolubles (including unconverted lignin) of the commercial zeolites evaluated.

Figure 2B:
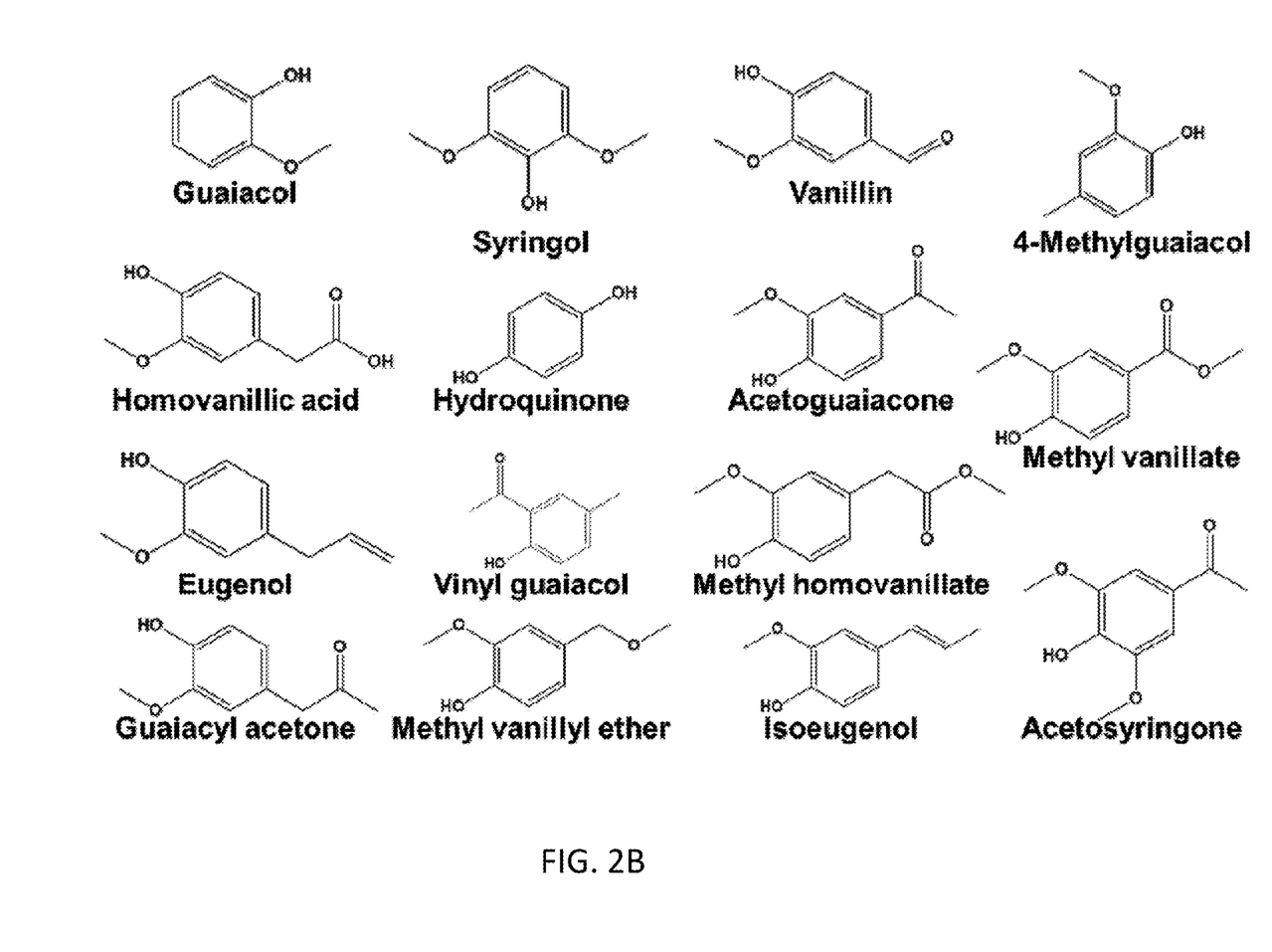
FIG. 2B provides the names and structures of the identified monomer products of FIG. 2A.

The complete product quantification along with the identified monomers for the thermal (without catalyst) and catalytic lignin depolymerization over H-ZSM-5 and Zr-KIT-5 catalysts is provided in Table 3, below. FIGS. 2A-2B also show the GC/MS spectrum for the catalytic lignin depolymerization over Zr-KIT-5(20) and the identified monomers.

TABLE 3

Quantification of Identified Monomers (mg monomers/g lignin)

| Monomer | Formula | Thermal | H-ZSM-5 (11.5) | Zr-KIT-5 (20) |
|---|---|---|---|---|
| 3-methoxybut-3-en-2-ol | $C_5H_{10}O_2$ | 3.97 | 7.34 | 7.8 |
| Methyl 2-hydroxyacetate | $C_3H_6O_3$ | 0.30 | 0.62 | 0.66 |
| Methyl furan-2-carboxylate | $C_6H_6O_3$ | 0.69 | 0.2 | 0.54 |
| dimethyl succinate | $C_6H_{10}O_4$ | 0.32 | 0.14 | 0.23 |
| 4-Methylguaiacol | $C_8H_{10}O_2$ | 0.26 | 0.17 | 0.20 |
| Dimethyl tetrahydrofuran-2,5-dicarboxylate | $C_8H_{12}O_5$ | 0.33 | 0.45 | 0.46 |
| Methyl Carbitol | $C_5H_{12}O_3$ | 0.26 | 0.62 | 0.53 |
| Guaiacol | $C_7H_8O_2$ | 4.24 | 2.97 | 4.06 |
| 4-Methylguaiacol | $C_8H_{10}O_2$ | 0.27 | 0.17 | 0.21 |
| methyl 1H-pyrrole-2-carboxylate | $C_6H_7NO_2$ | 0.05 | 0.10 | 0.05 |
| Eugenol | $C_{10}H_{12}O_2$ | 0.35 | 0.25 | 0.54 |
| 3-hydroxydihydrofuran-2(3H)-one | $C_4H_6O_3$ | 1.13 | 1.06 | 1.10 |
| Vinyl guaiacol | $C_9H_{10}O_2$ | 1.09 | 0.85 | 0.82 |
| Syringol | $C_8H_{10}O_3$ | 0.76 | 0.55 | 0.48 |
| Guaiacyl acetone | $C_9H_{12}O_3$ | 0.17 | 0.27 | 0.22 |
| Cis or trans-Isoeugenol | $C_{10}H_{12}O_2$ | 2.01 | 1.01 | 1.45 |
| Vanillin | $C_8H_8O_3$ | 9.88 | 12.42 | 16.75 |
| Methyl vanillate | $C_9H_{10}O_4$ | 1.30 | 3.22 | 3.69 |
| Acetoguaiacone | $C_9H_{10}O_3$ | 1.75 | 2.81 | 3.29 |
| Guaiacyl acetone | $C_{10}H_{12}O_3$ | 1.14 | 1.68 | 2.32 |
| Methyl homovanillate | $C_{10}H_{12}O_4$ | 0.74 | 1.02 | 1.02 |
| Acetosyringone | $C_{10}H_{12}O_4$ | 0.19 | 0.27 | 0.22 |
| Homovanillic acid | $C_9H_{10}O_4$ | 1.36 | 0.78 | 0.72 |
| Hydroquinone | $C_6H_6O_2$ | 1.17 | 5.04 | 7.24 |
| Total (mg/g) | | 33.72 | 44.01 | 54.6 |

The activity of the Zr-incorporated KIT and the H-ZSM-5 catalysts is summarized in Table 4, below. Lignin conversion is shown as $X_L$, as defined above. Table 4 shows the results of an additional experiment done using Zr-KIT-5 (20) but in which the lignin was first washed in water (as opposed to being used as is). It was unexpectedly found that the washed lignin produced significantly higher lignin conversion, significantly higher yields of THF soluble products and significantly lower yields of solid product residue. Without wishing to be bound by theory, it is thought that the improved performance is due to the removal of inorganics (e.g., $Na_2SO_4$). Such inorganics may effectively poison the catalyst. A typical procedure for washing lignin involves mixing 1 g of dealkaline lignin with 100 mL of water at room temperature and stirring for 5 minutes. The suspension is then filtered to remove water soluble inorganics and the lignin filtrand is washed with 2×20 ml water. The washed lignin is then dried in vacuo to remove moisture. In embodiments, other washing processes may be used, provide they reduce the level of inorganics in the lignin to, e.g., ≤5% by weight, ≤3% by weight, ≤1% by weight, etc. ("by weight" means compared to the lignin weight). The level of inorganics may be determined by thermogravimetric analysis (TGA). This experiment was repeated with the H-ZSM-5 catalyst. The yield of solid product residue was 27.5%.

TABLE 4

Activity of Zr-incorporated KIT catalysts and the H-ZSM-5 catalyst.[a]

| Catalyst | $X_L$ (%) | THF soluble products (%) | THF soluble identified monomers (%) | Solid product residue (%) | THF insolubles (including unconverted lignin) (%) | Mass balance (%) |
|---|---|---|---|---|---|---|
| Si-KIT-6 | 50.2 | 10.2 | 1.2 | 33.1 | 49.8 | 94.3 |
| Zr-KIT-6 (100) | 59.0 | 15.3 | 1.9 | 33.8 | 41.0 | 92.0 |
| Zr-KIT-6 (40) | 60.5 | 18.6 | 2.1 | 34 | 39.5 | 94.2 |
| Zr-KIT-6 (20) | 64.5 | 22.0 | 2.6 | 35.8 | 35.5 | 95.9 |
| Zr-KIT-5 (100) | 59.0 | 20.6 | 2.8 | 29.3 | 41.0 | 93.7 |
| Zr-KIT-5 (40) | 66.0 | 28.0 | 3.1 | 30.7 | 34.0 | 95.8 |
| Zr-KIT-5 (20) | 73.0 | 30.6 | 3.4 | 32.0 | 27.0 | 93.0 |
| Zr-KIT-5 (20) (using washed lignin) | 87.0 | 64.0 | 2.0 | 14.0 | 13.0 | 93.0 |
| H-ZSM-5 (11.5) | 78.5 | 27.1 | 3.2 | 41.0 | 21.5 | 92.8 |

[a]Reaction conditions: lignin (1.5 g), catalyst (0.1 g), water/methanol (⅕ v/v), 250° C., 30 min, 1000 rpm, 0.7 MPa of $N_2$ at ambient temperature.

Table 4 shows that all Zr incorporated KIT-6 catalysts were found to produce higher yields of THF soluble unidentified products, THF soluble identified monomers, and solid product residue as compared to Si-KIT-6. This can be attributed to an increase in the acidity of Zr based KIT-6 due to Zr incorporation. In both Zr-KIT-6 and Zr-KIT-5 catalysts, a decrease in Si/Zr ratio increased the yields of THF soluble unidentified products, THF soluble identified monomers, and solid product residue. On other hand, the yield of THF insolubles (including unconverted lignin) was found to decrease when the Si/Zr ratio of both Zr-KIT-6 and Zr-KIT-5 catalysts decreased. This can be attributed to the increase in acidity produced by the decrease in the Si/Zr ratio, which tends to convert lignin into THF soluble products and solid product residue.

The Zr-KIT-5(20) was found to have superior activity (30.6% yield of THF soluble products) compared to H-ZSM-5 (11.5) (27.1% yield of THF soluble products). Also, a comparable yield of identified monomers was obtained over Zr-KIT-5 (20) (3.4%) to that of H-ZSM-5 (11.5) (3.2%).

Further, the yield of solid product residue (41.0%) over H-ZSM-5(11.5) was greater than that observed with Zr-KIT-5 (20) (32.0%). This may be attributed to the fact that the micropores of H-ZSM-S(11.5) may hinder effective deconstruction of the bulky lignin to monomers. In contrast, the three-dimensional mesoporous nature of Zr-KIT-5 (20) facilitates effective breakdown of bulky molecules leading to a higher yield of monomers. Without wishing to be bound to any particular theory, it is also possible that the predominantly Brönsted acidic H-ZSM-S(11.5) may favor repolymerization of the formed monomers, leading to high yield of condensate. On the other hand, the dominant Lewis acidity of Zr-KIT-5 (20) may minimize repolymerization. Thus, Zr-KIT-5 (20) was found to be the best catalyst, with a 30.6% yield of THF soluble products and 3.4% yield of identified monomers, among the studied catalysts.

Characterizations of Lignin and Depolymerized Products

Figure 5:
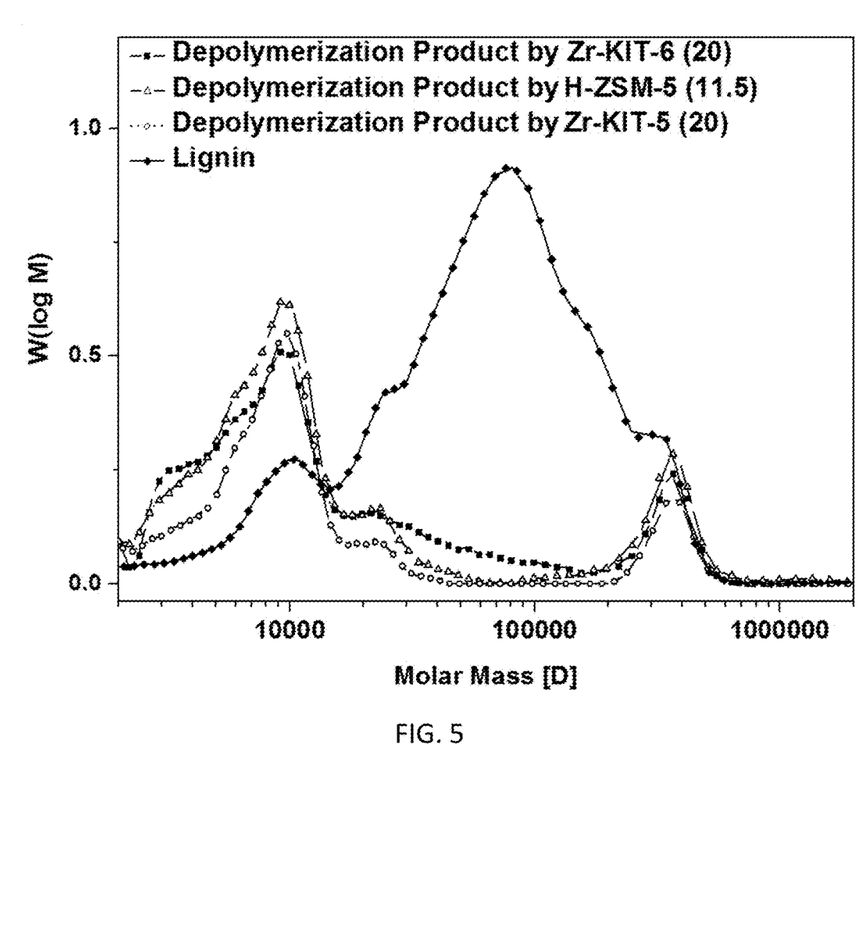
FIG. 5 shows Gel Permeation Chromatography (GPC) spectra of lignin and depolymerized products obtained over Zr-KIT-6 (20), H-ZSM-5 (11.5), and Zr-KIT-5 (20) catalysts.

As shown in FIG. 5, GPC spectra revealed a clear decrease in the molar mass of the depolymerized product mixture obtained from the various catalysts. However, unexpectedly, the product mixture from H-ZSM-5 (11.5) showed a significantly larger fraction of high molecular weight condensation products compared to the Zr-based catalysts, Zr-KIT-6 (20) and Zr-KIT-5 (20). The fraction of high molecular weight condensation products was quantified via the yield of insoluble products precipitating from the reaction mixture. The yield of insoluble products was as follows: Zr-KIT-6 (20) was 35.8 wt %; Zr-KIT-5 (20) was 32 wt %; and H-ZSM-5 (11.5) was 41.0 wt %. Again, without wishing to be bound to any particular theory, the microporous H-ZSM-5 (11.5) is predominantly Brönsted acidic and may favor repolymerization of the monomers formed. In contrast, the dominant Lewis acidity of Zr-based catalysts along with their ordered mesoporous structure may minimize repolymerization and coke formation, and thereby prolong catalyst activity. The ability to suppress repolymerization of formed monomers is an unexpected advantage of the Zr-based catalysts.

Other results further support these findings. Table 5, below, shows the C/H ratio of lignin and depolymerized products obtained over Zr-KIT-5 (20) and H-ZSM-S(11.5) catalysts. The C/H ratios of benzene, toluene and xylene are shown for reference. The C/H ratio was found to be in range of aromatic for THF soluble products and THF insolubles. Solid product residue indicated char with higher C/H ratio. As discussed above, predominantly Brönsted acidic H-ZSM-5(11.5) may favor re-polymerization of the formed monomers leading to high yield of condensate with high C/H ratio.

TABLE 5

C/H ratio of lignin and depolymerized products obtained over Zr-KIT-5(2) and H-ZSM-5(11.5) catalysts.

| | C/H ratio obtained over | |
|---|---|---|
| Depolymerized Products | Zr-KIT-5(20) | H-ZSM-5(11.5) |
| THF soluble products | 8.5 | 8.5 |
| THF insolubles | 8.6 | 8.6 |
| Solid product residue | 10.5 | 11.3 |

C/H ratios: Lignin = 9.4, Benzene = 12, Toluene = 10.5 and Xylene = 9.6.

NMR Results $^1$H NMR spectra of lignin and of the THF soluble depolymerized product mixture obtained over Zr-KIT-5(20) and H-ZSM-5(11.5) catalysts were collected (data not shown). Chemical shifts observed around 0.80-1.50 ppm were attributed to primary, secondary and tertiary alkyl groups.[31] The Ar—C(CH$_3$)$_3$ methyl proton was observed in both lignin and THF soluble products at 1.24 ppm. Typically, benzylic protons (Ar—CH$_3$) and the protons associated with carbonyl groups (Ar—CO—CH$_3$) and ester groups (Ar/R—CH$_2$—COOR/Ar) are observed at 1.6-2.7 ppm. The peaks observed at 1.9 and 2.5 ppm in lignin and at 1.64, 2.14, 2.45, 2.56 ppm in depolymerized product can be attributed to benzylic or carbonyl or ester groups. The peak at 3.83 or 3.8 ppm in both lignin and depolymerized product indicates an ester group (Ar/R—COOCH$_2$R/Ar).[31] Additional new peaks observed at 3.71 ppm in the THF soluble products can be attributed to the substitution of —OCH$_3$ in aromatic ring. Peaks appearing at 5.0-5.5 ppm in the product sample can be assigned to alkene groups. Peaks observed between 6.5 to 8.5 ppm are assigned to aromatic protons. Peaks due to aldehydes appeared at 9.77 ppm in lignin and at 9.77 and 9.62 ppm in the depolymerized THF soluble product sample.

2D Heteronuclear Single Quantum Correlation (HSQC) NMR spectra of the dealkaline lignin starting material and of THF soluble products obtained over Zr-KIT-5(20) were also collected (data not shown). For dealkaline lignin, the chemical shift observed in the 3-5.5 ppm ($^1$H) and 50-90 ppm ($^{13}$C) regions are attributed to β-β, β-O-4, β-5 and α-O-4 inter unit linkages in lignin.[39] Peaks observed between 6-8 ppm ($^1$H) and 100-140 ppm ($^{13}$C) correspond to the aromatic region of respective subunit. The chemical shift in region of 3.2-4.2 ppm ($^1$H), 56-58 ppm ($^{13}$C) correlated to the different methoxy-linkages of syringyl or guaiacyl subunits.

For the THF soluble products obtained over Zr-KIT-5 (20), the signals belonging to aliphatic region corresponding to guaiacolics and alkylphenolics were found to be remarkably increased. New peaks corresponding to alkenes attached to aromatic side chains were observed in product sample. Moreover, aromatic regions corresponding to guaiacolics and phenolics were observed in depolymerized products. In addition, new signals belonging to aldehyde appeared in depolymerized product samples. These results confirm that catalytic depolymerization led to cleaving of interunit linkages of lignin to produce aromatic monomers, as confirmed by GC-MS (described above).

Thermal Degradation Results

The thermal degradation (TGA-DTA) studies of lignin (untreated) and depolymerized products were carried out in the presence of air at temperatures up to 1000° C. (data not shown). The moisture content of lignin was calculated on the basis of the weight loss until 150° C. and found to be 11%. Thermal degradation of untreated lignin and THF insolubles (including unreacted lignin) and 14% of unburnt residue were observed. Thermal degradation of THF soluble products led to 3% of unburnt residue. Solid product residue including catalyst yielded 27% of unburnt residue. A similar quantity (14%) of inorganic residue (ash) was obtained after lignin calcination at 650° C., for 6 h. In order to identify the composition of the inorganic residue (ash), XRD analysis was performed.

XRD patterns of untreated lignin and inorganic residue (ash) were obtained and analyzed (data not shown). From the XRD analysis, it is clear that the inorganic residue (ash) is composed of $Na_2SO_4$, in accordance with reported literature.[31] Absence of peaks for amorphous cellulose (2θ=17.7-18.5°) and for crystalline cellulose (2θ=22.5°) confirmed that the lignin was devoid of cellulose contamination.[31]

Study of the Stability and Characterization of Zr-KIT-5 (20) Catalyst

In order to design a robust catalyst for depolymerization, the stability of the catalyst is of paramount importance. The catalysts reported in the literature for lignin depolymerization have not been thoroughly analyzed for their stability. Thus, the stability of mesoporous silicate along with its physicochemical characterizations were examined. Due to the higher activity of Zr-KIT-5(20) for lignin depolymerization, this catalyst was selected for further evaluation for stability. The stability of the catalysts was first evaluated using two different solvent systems: water and water/methanol (1/5 v/v) without lignin. Since the lignin depolymerization reaction was carried in a methanol+water solvent, it followed that catalyst stability should be evaluated in the same solvent system under similar reaction conditions. Typically, the desired quantity of catalyst with solvent was added in 300 mL batch reactor (Parr Instruments) and heated to the desired temperature. Once the desired temperature was reached, the stirring was set to 1000 rpm and continued for 30 min. The reactor was then cooled with ice water and the catalyst was separated from the solvent by filtration. The catalyst obtained was dried and calcined at 550° C. for 5 h. The calcined catalyst was characterized by XRD, $N_2$ physisorption and $NH_3$-TPD. The results are summarized in Table 6, below. The first two rows of Table 6 provide the physical characteristics of the Zr-KIT-6(20) and Zr-KIT-5 (20) catalysts, respectively. The remaining rows of Table 6 provide the physical characteristics of the Zr-KIT-5(20) catalyst after being subjected to the various conditions indicated.

TABLE 6

Physical characteristics of Zr-incorporated KIT catalysts and results of stability experiments for Zr-KIT-5(20) catalyst.

| Catalyst | $S_{BET}$ $(m^2/g)^a$ | $V_{p, BJH}$ $(nm)^b$ | $d_{p, BJH}$ $(cm^3/g)^c$ | Total acidity $(mmol/g)^d$ |
|---|---|---|---|---|
| Zr-KIT-6(20) | 810 | 1.07 | 9.3 | 0.50 |
| Zr-KIT-5(20) | 970 | 0.81 | 8.7 | 0.64 |
| 100° C. - MeOH + $H_2O$ | 891 | 0.75 | 3.4 | 0.50 |
| 150° C. - MeOH + $H_2O$ | 871 | 0.75 | 3.4 | 0.54 |
| 200° C. - MeOH + $H_2O$ | 874 | 0.77 | 3.5 | 0.60 |
| 250° C. - MeOH + $H_2O$ | 618 | 0.75 | 4.9 | 0.48 |
| 250° C. - $H_2O$ | 273 | 1.04 | 15.3 | |
| 250° C. - After reaction | 61 | 0.17 | 11.5 | 0.05 |
| 200° C. - After reaction | 265 | 0.32 | 3.8 | 0.11 |

$^a S_{BET}$ = specific surface area,
$^b V_{P, BJH}$ = total pore volume,
$^c d_{P, BJH}$ = BJH adsorption average pore diameter.
$^d$Total acidity of catalyst was determined with $NH_3$-TPD.

The $N_2$ adsorption-desorption isotherm of fresh Zr-KIT-5(20) exhibited type IV adsorption isotherm, and showed a sharp capillary condensation occurring between 0.60 and 0.70 $P/P_0$ and a broad $H_2$-type hysteresis loop with desorption occurring at ~0.47 $P/P_0$.[36] When the temperature increased from 100 to 250° C. in the methanol+water treated catalyst, the desorption isotherm shifted to much lower $P/P_0$ values. However, the isotherms from catalyst treated at 100° C., 150° C. and 200° C. were typical of ordered mesoporous materials like parent Zr-KIT-5 (20), possessing large uniform cage-like pores.[36] All of the methanol+water treated catalysts exhibited significantly different slope of the capillary condensation step than the fresh Zr-KIT-5 (20) catalyst. In addition, all the treated samples showed a decrease in micropore volume ($V_p$) compared to the parent Zr-KIT-5 (20). Similarly, surface area was found to be decreased with an increase in treatment temperature. However, the catalyst treated at 250° C. in both water and methanol+water solvent showed significantly different isotherms and significant decrease in surface area than the parent catalyst. Used catalyst recovered after lignin depolymerization at 250° C. exhibited a noticeable decrease in surface area, acidity and collapse of the pore structure.

Catalyst treated in methanol+water at temperature 200° C. and below maintained mesoporous structure. Thus, in order to check the catalyst stability for lignin depolymerization, lignin depolymerization was carried out over Zr-KIT-5(20) at 200° C. The used catalyst recovered after lignin depolymerization at 200° C., showed a significant decrease in surface area, acidity and collapse of the porous structure. Although catalyst was stable in the solvent system alone at 200° C., it was not stable for actual lignin depolymerization under the same conditions. This may be attributed to the inorganic residue (Na$_2$SO$_4$) present in the lignin, which tended to deactivate the catalyst and collapse the structure.

CONCLUSIONS

The Zr-incorporated mesoporous silicates show superior performance for lignin depolymerization compared to published reports with other acidic catalysts, yielding phenolic monomers that are promising precursors for upgrading to aromatic chemicals and fuels.

REFERENCES

1. Bruijnincx P C A, Rinaldi R, Weckhuysen B M. Unlocking the potential of a sleeping giant: lignins as sustainable raw materials for renewable fuels, chemicals and materials. *Green Chem.* 2015; 17(11):4860-4861.
2. Xu C P, Arancon R A D, Labidi J, Luque R. Lignin depolymerisation strategies: towards valuable chemicals and fuels. *Chem Soc Rev.* Nov. 21, 2014; 43(22):7485-7500.
3. Shen X J, Wang B, Huang P L, Wen J L, Sun R C. Understanding the structural changes and depolymerization of *Eucalyptus* lignin under mild conditions in aqueous AlCl3. *Rsc Advances.* 2016; 6(51):45315-45325.
4. Singh S K, Nandeshwar K, Ekhe J D. Thermochemical lignin depolymerization and conversion to aromatics in subcritical methanol: effects of catalytic conditions. *New J Chem.* 2016; 40(4):3677-3685.
5. Zakzeski J, Bruijnincx P C A, Jongerius A L, Weckhuysen B M. The Catalytic Valorization of Lignin for the Production of Renewable Chemicals. *Chem Rev.* June 2010; 110(6):3552-3599.
6. Kruger J S, Cleveland N S, Zhang S T, et al. Lignin Depolymerization with Nitrate-Intercalated Hydrotalcite Catalysts. *Acs Catal.* February 2016; 6(2):1316-1328.
7. Song Q, Wang F, Xu J. Hydrogenolysis of lignosulfonate into phenols over heterogeneous nickel catalysts. *Chem Commun.* 2012; 48(56):7019-7021.
8. Galkin M V, Sawadjoon S, Rohde V, Dawange M, Samec J S M. Mild Heterogeneous Palladium-Catalyzed Cleavage of beta-O-4'-Ether Linkages of Lignin Model Compounds and Native Lignin in Air. *Chemcatchem.* January 2014; 6(1):179-184.
9. Wang X Y, Rinaldi R. A Route for Lignin and Bio-Oil Conversion: Dehydroxylation of Phenols into Arenes by Catalytic Tandem Reactions. *Angewandte Chemie-International Edition.* Oct. 25, 2013; 52(44):11499-11503.
10. Luo H, Klein I M, Jiang Y, et al. Total Utilization of *Miscanthus* Biomass, Lignin and Carbohydrates, Using Earth Abundant Nickel Catalyst. *Acs Sustainable Chemistry & Engineering.* April 2016; 4(4):2316-2322.
11. Zakzeski J, Jongerius A L, Bruijnincx P C A, Weckhuysen B M. Catalytic Lignin Valorization Process for the Production of Aromatic Chemicals and Hydrogen. *Chemsuschem.* 2012; 5(8): 1602-1609.
12. Song Q, Wang F, Cai J Y, et al. Lignin depolymerization (LDP) in alcohol over nickel-based catalysts via a fragmentation-hydrogenolysis process. *Energ Environ Sci.* March 2013; 6(3):994-1007.
13. Klein I, Saha B, Abu-Omar M M. Lignin depolymerization over Ni/C catalyst in methanol, a continuation: effect of substrate and catalyst loading. *Catal Sci Technol.* 2015; 5(6):3242-3245.
14. Xu W Y, Miller S J, Agrawal P K, Jones C W. Depolymerization and Hydrodeoxygenation of Switchgrass Lignin with Formic Acid. *Chemsuschem.* 2012; 5(4):667-675.
15. Crestini C, Caponi M C, Argyropoulos D S, Saladino R. Immobilized methyltrioxo rhenium (MTO)/H2O2 systems for the oxidation of lignin and lignin model compounds. *Bioorganic & Medicinal Chemistry.* Aug. 1, 2006; 14(15):5292-5302.
16. Sales F G, Maranhao L C A, Lima N M, Abreu C A M. Experimental evaluation and continuous catalytic process for fine aldehyde production from lignin. *Chem Eng Sci.* September-October 2007; 62(18-20):5386-5391.
17. Prado R, Brandt A, Erdocia X, Hallet J, Welton T, Labidi J. Lignin oxidation and depolymerisation in ionic liquids. *Green Chem.* 2016; 18(3):834-841.
18. Widyaya V T, Vo H T, Dahnum D, Lee H. Magnesium Oxide-catalyzed Oxidative Depolymerization of EFB Lignin. *B Korean Chem Soc.* April 2016; 37(4):515-521.
19. Zhang J, Deng H, Lin L. Wet Aerobic Oxidation of Lignin into Aromatic Aldehydes Catalysed by a Perovskite-type Oxide: LaFe(1-x)Cu(x)O(3) (x=0, 0.1, 0.2). *Molecules.* August 2009; 14(8):2747-2757.
20. Ouyang X P, Ruan T, Qiu X Q. Effect of solvent on hydrothermal oxidation depolymerization of lignin for the production of monophenolic compounds. *Fuel Process Technol.* April 2016; 144:181-185.
21. Nguyen J D, Matsuura B S, Stephenson C R J. A Photochemical Strategy for Lignin Degradation at Room Temperature. *J Am Chem Soc.* Jan. 29, 2014; 136(4):1218-1221.
22. vom Stein T, Weigand T, Merkens C, Klankermayer J, Leitner W. Trimethylenemethane-Ruthenium(II)-Triphos Complexes as Highly Active Catalysts for Catalytic CO Bond Cleavage Reactions of Lignin Model Compounds. *Chemcatchem.* February 2013; 5(2):439-441.
23. Sedai B, Diaz-Urrutia C, Baker R T, Wu R, Silks L A P, Hanson S K. Aerobic Oxidation of beta-1 Lignin Model Compounds with Copper and Oxovanadium Catalysts. *Acs Catal.* December 2013; 3 (12):3111-3122.
24. Son S, Toste F D. Non-Oxidative Vanadium-Catalyzed C—O Bond Cleavage: Application to Degradation of Lignin Model Compounds. *Angew Chem Int Edit.* 2010 2010; 49(22):3791-3794.
25. Nichols J M, Bishop L M, Bergman R G, Ellman J A. Catalytic C—O Bond Cleavage of 2-Aryloxy-1-arylethanols and Its Application to the Depolymerization of Lignin-Related Polymers (vol 132, pg 12554, 2010). *J Am Chem Soc.* Nov. 24, 2010; 132(46): 16725-16725.
26. Rahimi A, Azarpira A, Kim H, Ralph J, Stahl S S. Chemoselective Metal-Free Aerobic Alcohol Oxidation in Lignin. *J Am Chem Soc.* May 1, 2013; 135(17):6415-6418.
27. Gao Y, Zhang J, Chen X, Ma D, Yan N. A Metal-Free, Carbon-Based Catalytic System for the Oxidation of Lignin Model Compounds and Lignin. *Chempluschem.* June 2014; 79(6):825-834.
28. Vigneault A, Johnson D K, Chornet E. Base-catalyzed depolymerization of lignin: Separation of monomers. *Canadian Journal of Chemical Engineering.* December 2007; 85(6):906-916.
29. Roberts V M, Stein V, Reiner T, Lemonidou A, Li X B, Lercher J A. Towards Quantitative Catalytic Lignin Depolymerization. *Chem-Eur J.* May 2011; 17(21):5939-5948.
30. Lankau T, Yu C H. Intermediate oxiranes in the base-catalyzed depolymerisation of lignin. *Green Chem.* 2016; 18(6): 1590-1596.
31. Deepa A K, Dhepe P L. Lignin Depolymerization into Aromatic Monomers over Solid Acid Catalysts. *Acs Catal.* January 2015; 5(1):365-379.

32. Matson T D, Barta K, Iretskii A V, Ford P C. One-Pot Catalytic Conversion of Cellulose and of Woody Biomass Solids to Liquid Fuels. *J Am Chem Soc.* Sep. 7, 2011; 133(35):14090-14097.
33. Warner G, Hansen T S, Riisager A, Beach E S, Barta K, Anastas P T. Depolymerization of organosolv lignin using doped porous metal oxides in supercritical methanol. *Bioresource Technology.* June 2014; 161:78-83.
34. Sturgeon M R, Kim S, Lawrence K, et al. A Mechanistic Investigation of Acid-Catalyzed Cleavage of Aryl-Ether Linkages: Implications for Lignin Depolymerization in Acidic Environments. *Acs Sustainable Chemistry & Engineering.* March 2014; 2(3):472-485.
35. Kong J C, He M Y, Lercher J A, Zhao C. Direct production of naphthenes and paraffins from lignin. *Chem Commun.* 2015; 51(99):17580-17583.
36. Ramanathan A, Zhu H D, Maheswari R, Subramaniam B. Novel zirconium containing cage type silicate (Zr-KIT-5): An efficient Friedel-Crafts alkylation catalyst. *Chem Eng J.* Oct. 15, 2015; 278:113-121.
37. Pan Q, Ramanathan A, Snavely W K, Chaudhari R V, Subramaniam B. Synthesis and Dehydration Activity of Novel Lewis Acidic Ordered Mesoporous Silicate: Zr-KIT-6. *Industrial & Engineering Chemistry Research.* Nov. 6, 2013; 52(44):15481-15487.
38. Ramanathan A, Subramaniam B, Maheswari R, Hanefeld U. Synthesis and characterization of Zirconium incorporated ultra large pore mesoporous silicate, Zr-KIT-6. *Micropor Mesopor Mat.* Feb. 2, 2013; 167:207-212.
39. Narani A, Chowdari R K, Cannilla C, et al. Efficient catalytic hydrotreatment of Kraft lignin to alkylphenolics using supported NiW and NiMo catalysts in supercritical methanol. *Green Chem.* 2015; 17(11): 5046-5057.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A process for depolymerizing lignin, the process comprising exposing a liquid feed comprising lignin and a solvent to a metal-incorporated solid mesoporous silicate catalyst under conditions sufficient to depolymerize the lignin to produce one or more aromatic monomers,
wherein the metal-incorporated solid mesoporous silicate catalyst is M-KIT-5, M-KIT-6, or combinations thereof,
wherein M is Zr, Nb, W, Al or combinations thereof,
and wherein the lignin is washed prior to use in the process.

2. The process of claim 1, wherein the metal-incorporated solid mesoporous silicate catalyst has a pore diameter $d_{p,BJH}$ of greater than about 6 nm.

3. The process of claim 2, wherein the pore diameter is in the range of from about 6 nm to about 11 nm.

4. The process of claim 1, wherein the metal-incorporated solid mesoporous silicate catalyst is characterized by a maximum total acidity for the selected metal.

5. The process of claim 1, wherein M is Zr.

6. The process of claim 1, wherein the liquid feed is substantially free of biopolymers other than the lignin.

7. The process of claim 1, wherein the conditions include an inert atmosphere substantially free of $H_2$, $O_2$, and $H_2O_2$.

8. The process of claim 1, wherein the lignin is dealkaline lignin.

9. The process of claim 1, wherein the process provides a yield of products including the one or more aromatic monomers soluble in an organic solvent of at least 60% by weight.

10. The process of claim 1, wherein the process provides a yield of solid product residue of no more than 15% by weight.

11. The process of claim 1, wherein M is Zr and wherein the metal-incorporated solid mesoporous silicate catalyst is characterized by a maximum total acidity.

12. The process of claim 11, wherein the process provides a yield of products including the one or more aromatic monomers soluble in an organic solvent of at least 60% by weight and a yield of solid product residue of no more than 15% by weight.

13. The process of claim 1, wherein the metal-incorporated solid mesoporous silicate catalyst is Zr-KIT-5 and is characterized by a maximum total acidity.

14. The process of claim 13, wherein the process provides a yield of products including the one or more aromatic monomers soluble in an organic solvent of at least 60% by weight and a yield of solid product residue of no more than 15% by weight.

* * * * *